United States Patent [19]

Yamazaki

[11] Patent Number: 5,026,828
[45] Date of Patent: * Jun. 25, 1991

[54] METHOD OF PURIFYING RECOMBINANT PRES-1/S-2/S/S HEPATITIS B ANTIGEN FROM YEAST

[75] Inventor: Shigeko Yamazaki, Hatfield, Pa.

[73] Assignee: Merck & Co., Inc., Rahway, N.J.

[*] Notice: The portion of the term of this patent subsequent to Apr. 30, 2008 has been disclaimed.

[21] Appl. No.: 279,323

[22] Filed: Dec. 1, 1988

Related U.S. Application Data

[63] Continuation of Ser. No. 19,820, Feb. 27, 1987, abandoned.

[51] Int. Cl.⁵ .................................................. C07K 3/26
[52] U.S. Cl. .................................... 530/414; 530/412; 530/418; 530/419; 530/422; 530/300; 530/350; 530/824; 424/89
[58] Field of Search ............... 530/412, 414, 497, 402, 530/419, 824, 820, 418, 371; 435/68, 70

[56] References Cited

U.S. PATENT DOCUMENTS

| | | | |
|---|---|---|---|
| 4,017,360 | 5/1975 | Bertland et al. | 424/89 |
| 4,578,269 | 3/1986 | Morein | 424/89 |
| 4,612,283 | 10/1984 | Sugahara et al. | 435/68 |
| 4,624,918 | 11/1986 | Hersberg | 424/89 |
| 4,649,192 | 5/1986 | Van Wijnendaele et al. | 530/371 |
| 4,666,713 | 5/1987 | Skelly et al. | 424/89 |
| 4,683,293 | 7/1987 | Wang | 424/89 |
| 4,683,294 | 7/1987 | Wynendaele et al. | 429/89 |
| 4,855,055 | 8/1989 | Lin et al. | 424/89 |
| 4,894,444 | 1/1990 | Scuttergood et al. | 530/412 |
| 4,902,783 | 2/1990 | Goda et al. | 530/412 |

FOREIGN PATENT DOCUMENTS

| | | | |
|---|---|---|---|
| 072318 | 2/1983 | European Pat. Off. | |
| 105149 | 4/1984 | European Pat. Off. | |
| 0114506 | 8/1984 | European Pat. Off. | 435/68 |
| 171908 | 2/1986 | European Pat. Off. | |
| 198474 | 10/1986 | European Pat. Off. | |
| 226846 | 11/1986 | European Pat. Off. | |
| WO87/01128 | 2/1987 | PCT Int'l Appl. | |

OTHER PUBLICATIONS

Itoh, Y. et al., Biochem. Biophys. Res. Comm. 138, 268 (1986).
Hitzeman, R. A. et al., Nucleic Acids Res. 11, 2745 (1983).
Meyhack et al, Chem. Abst. 1985, vol. 103, #136419w.
Holm et al, Gene, 1986, pp. 169-173, vol. 42.
Pharmacia Bulletin #50-01-339, 1986 (vol. 13.6).
Neurath et al, Nature, 315, 1985, pp. 154-157.
Sofer et al, BioTechniques, Nov./Dec. 1983, pp. 198-203.
P. Tiollais et al., Science 213:406-411 (1981).
D. R. Milich et al., PNAS 82:8168-8172 (1985).
A. R. Neurath, Science 224:392-394 (1984).
A. R. Neurath, Nature 315:154-156 (1985).
A. Machida, Gastroenterology 86:910-918 (1984).
E. Elfassi et al., J. Theor. Biol. 121:371-374 (1986).
J. A. Waters et al., Journal of Med. Virology 19:79-86 (1986).
J. A. Waters et al., Journal of Hepatitis, 0 Suppl. 1, 301 (1985).
B. J. Randle et al., J. of Immunological Methods 77:25-36 (1985).
Amicon-a Grace Company-Diaflo Hollow Fiber Cartridges Pub. No. 1-116D.
A/G Technology Corporation-Innovative Hollow Fiber Membrane Tech., 13 pages.
Microgon—The Unique Microfilter Designed for Difficult Solutions, 14 pages.
Biologics Technical Information CHAPS/CHAPSO-220201 and 220202.
Wampler et al, PNAS, vol. 82, 1985, pp. 6830-6834.
Hanioda, CA vol. 104, 1986, #33033f.
Van Wignenluele et al., CA vol. 106, 1987, #17020m.
Van Wynendaele et al., CA vol. 106, 1987, #90157r.

Primary Examiner—Garnette D. Draper
Attorney, Agent, or Firm—Roy D. Meredith; Charles M. Caruso

[57] ABSTRACT

Recombinant hepatitis B antigen bound to yeast membranes in yeast expression systems is rapidly purified by subjecting the membrane bound protein to agents that release undesired proteins, followed by agents that release the recombinant hepatitis B antigen.

8 Claims, 2 Drawing Sheets

METHOD OF PURIFYING RECOMBINANT PRES-1/S-2/S HEPATITIS B ANTIGEN FROM YEAST

This is a continuation of application Ser. No. 19,820, filed Feb. 27, 1987, now abandoned.

INTRODUCTION

Hepatitis B surface antiqen often occurs as a glycoprotein-protein complex that confers immunity against the pathological effects of subsequent infection by hepatitis B virus. Sources for safe, rapid and inexpensive manufacture of the antigen for vaccination purposes have been limited to serum or plasma from patients who synthesize large quantities of the requisite antigen, usually in the form of 22 nm particles. With the advent of recombinant DNA techniques, DNA coding for the surface antigen is inserted into yeast, E. coli and other cellular systems, then expressed. The resulting polypeptide product varies substantially with the DNA construction used as well as the host or cellular systems employed to express the inserted DNA.

The HB virion is composed of two groups of structural proteins, the core proteins and the envelope or surface ("S") proteins. In addition to being the major surface proteins of the virion, i.e., Dane particle, the "S" proteins are the sole constituents of Australia antigen, or 22 nm particles. The "S" proteins are the translational products of a large open reading frame (ORF) encoding 389-400 amino acids, depending upon serotype. This ORF is demarcated into three domains, each of which begins with an ATG codon that is capable of functioning as a translational initiation site in vivo. These domains are referred to as preS-1 (108-119- amino acids) preS-2 (55 amino acids), and S (226 amino acids) in their respective 5'-3' order in the gene. The six protein products derived from this ORF have the following compositions:

1) gp42 (42,000 dalton glycoprotein)=preS-1/S-2/S (meaning preS-1 contiguous with preS-2, contiguous with S),
2) p39 (p=protein)=preS-1/S-2/S,
3) gp36=preS-2/S (two glycosylation sites),
4) gp33 =preS-2/S (one glycosylation site),
5) gp27 =S (one glycosylation site),
6) p24 =S.

All six proteins are present to an approximately equimolar extent in the HBV Dane particle. In the 22 nm particle, the 4 smaller Proteins are present to an approximately equimolar extent, while gp42 and p39 are present in at most one or a few molecules per particle. The preS-1 and PreS-2 regions may have functions of promoting secretion of the S region. For reviews of these fundamental properties of the protein, see Tiollais, P. et al., Science 213, 406 (1981) and Milich, D. R. et al., Proc. Natl. Acad. Sci. 82, 8168 (1985).

The preS-2 region of the hepatitis B antigen comprises about 55AA residues. Its presence provides a dominant epitope that is more immunogenic in vivo than epitopes of the S protein, according to Neurath, A. R. et al., Science 224, 392 (1984), Neurath, A. R. et al., Nature 315, 154 (1985), and Milich, D. R. et al., supra. The preS-2 polypeptide also has receptor-like properties for polymerized human serum albumin (pHSA), a trait also possessed by liver cells which are known to bind pHSA, Machida, A. et al., Gastroenterology 86, 910 (1984).

Since the presence of preS-2 sequences in the surface antigen is a desirable property for the purposes of immunization, expression systems have been developed for the expression of preS-1S-2/S protein and other variants. See, example, U.S. Pat. No. 824,405, filed Jan. 31, 1986, now U.S. Pat. No. 4,816,564. The present invention is directed to rapid methods of purifying the preS-1/S-2/S proteins and any variants that are membrane-bound a yeast expression on system. These new method involve essentially a two-step process of initially removing unwanted proteins from the yeast membrane, followed by removal and isolation of the preS-1/S-2/S protein from the membrane in substantial form. It will be appreciated that the present relates to a method of purifying a protein inserted or otherwise bound to a system having no natural relation to the protein.

Purification of recombinant not infrequently require new methods or novel combinations of old methods, since the composition the source for recombinant forms e.g. yeast are different from conventional sources e.g. serum. One cannot predict what methods are useful for isolating proteins from recombinant cell cultures on the basis of the knowledge and know-how of methods useful isolating proteins from classical or otherwise conventional sources. Purification processes designed for preparing vaccines require unusual purity in the product, another indication of the unpredictability in the art. For a similar new, see U.S. Pat. No. 4,624,918.

BRIEF DESCRIPTION OF THE INVENTION

A method of substantial purifying recombinant preS-1/S-2/S hepatitis B antigen, or portion thereof, from yeast membranes, comprising the steps of a) taking a portion of yeast membrane associated antigen extract;

b) removing the debris of the extract of step (a) by centrifugation;

c) subjecting the to diafiltration in the presence of a solution effective to release undesired yeast proteins, and thereafter removing said undesired membrane-bound proteins;

d) subjecting the produce step (c) to a second solution effective to release surface antigen;

e) subjecting the surface released in step (d) to diafiltration;

f) subjecting the filtrate step (e) to diafiltration to remove low molecular weight impurities, resulting in a substantially purified recombinant preS-1/S-2/S hepatitis B , or portion thereof.

DEFINITIONS AND ABBREVIATIONS

Figure 1:
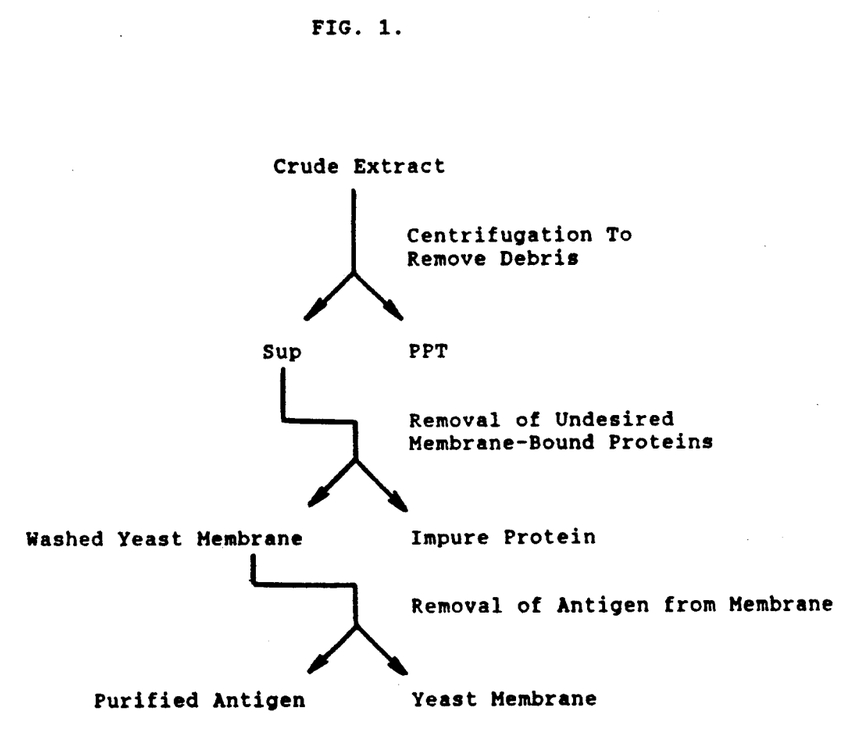
FIG. 1. Schematic diagram of for purifying membrane-bound proteins
Figure 2:
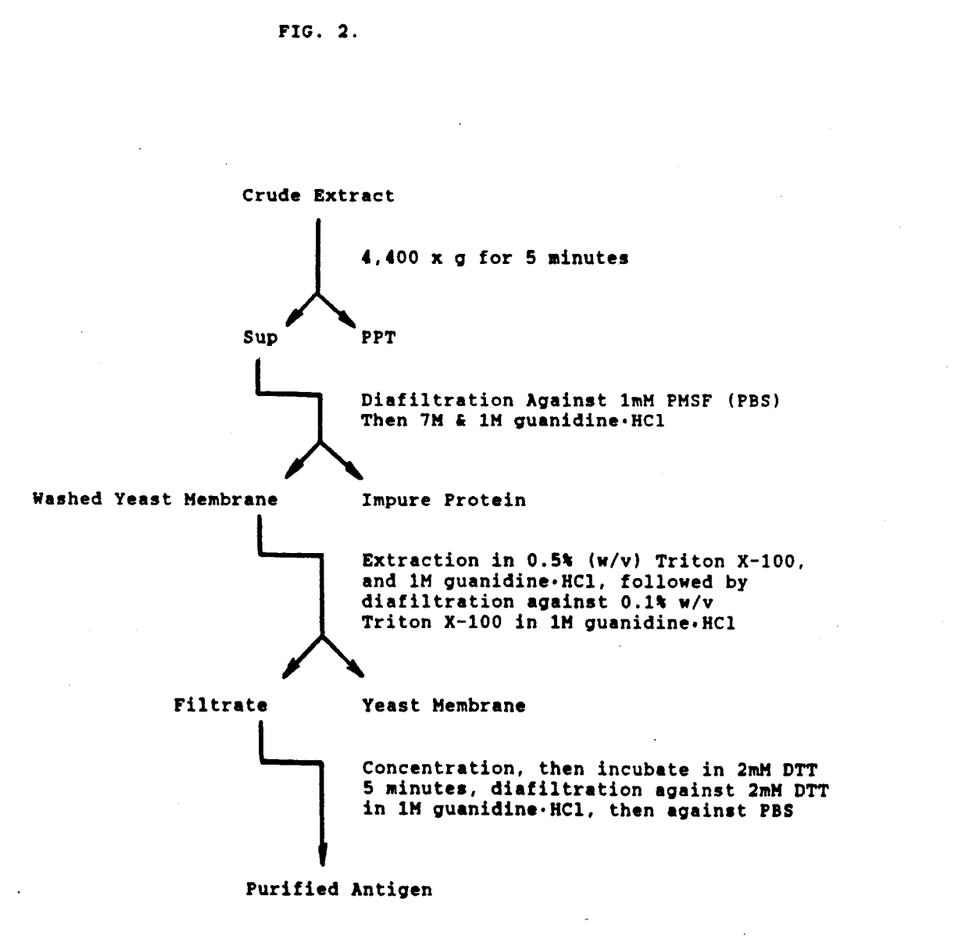
FIG. 2. Schematic diagram illustrating some of the preferred in the method of purifying PreS-1/S-2/S protein from yeast membranes.

Specific activity: a weight-to-weight rat of immunochemically reactive sAg to total protein.

| | |
|---|---|
| AA | amino acid |
| DNA | deoxyribonucleic acid |
| DTT | dithiothreitol |
| ED$_{50}$ | 50% effective dose |
| EDTA | ethylenediamine tetraacetic acid trisodium salt |

| | |
|---|---|
| L | liter |
| MB | membrane-bound |
| Mr | mobility |
| MW | molecular weight |
| NMW | nominal molecular weight cutoff |
| pHSA | polymerized human serum albumin |
| PBS | phosphate buffered saline, 0.15 M NaCl in 7 mM sodium phosphate buffer, pH about 7.2 |
| PMA | protective monoclonal antibodies |
| PMSF | phenylmethylsulfonyl fluoride |
| PPT | precipitate |
| psi | pounds per square inch |
| S | surface |
| SDS-PAGE | sodium dodecyl sulfate polyacrylamide gel electrophoresis |
| Sup | supernatant |

DETAILED DESCRIPTION OF THE INVENTION

The processes of the present invention involve new methods of purifying membrane-bound (MB) hepatitis B surface antigen from yeast extracts. Undesired MB proteins are released by treatment with agents including chaotropic agents, then the MB surface antigen is released by another solution containing neutral detergents or chaotropic agents, or combinations thereof.

It will be understood that the novel purification processes of the present invention are applicable to a range of expressed MB proteins. One principle example is yeast cells transformed by yeast vector YADH2/PSSC-1. This system expresses a preS1/S-2/S amino acid sequence which promotes binding to yeast membranes. Other variant amino acid sequences at the amino terminal end of the S protein, including variations in the preS-1 or preS-2 regions, will have the same effect of associating the contiguous S region amino acid sequence with a yeast membrane. The processes of the present invention are designed to provide rapid and efficient methods of purifying these preS-1/S-2/S protein variants in accordance with the principles of the present invention. For example, conservative substitutions in the preS-1/S-2/S amino acid sequence generally will not result in any substantial or novel modification of the principles and practice of the present invention. Conservative substitutions are known; see Elfassi, E. et al., *J. Theor. Biol.* 121, 371 (1986). Alternatively, deletions within the S region or at the carboxy terminal end of the S region will not in general require any modifications of the processes for purification discussed herein. It will be understood that membrane-bound surface antigen, or portion thereof includes any such variations in the amino acid sequence, whether by conservative amino acid substitution, deletion, or other process, provided that the surface antigen or portion thereof, after purification from its membrane-bound state, is immunochemically reactive with antibodies specific for the preS-1/S-2/S protein, the 22 nm particle, Australia antigen, or other natural form of the hepatitis surface antigen sequence.

Many yeast expression systems are clearly adequate for providing sources of the MB surface antigen. The *S. cerevisiae strain* 2150-3-2 transformed with YADH2/PSSC-1 in Example 1 is intended as a merely incidental source. Other yeast vectors include but are not limited to shuttle vectors, cosmid plasmids, chimeric plasmids, and those having sequences derived from 2-micron circle plasmids. A variety of promoters and other yeast transcriptional control sequences may be used to express the inserted DNA sequence coding for surface antigen, including those of GAL10 and the alpha mating factor.

The genus Saccharomyces is composed of a variety of species. Most commonly used is *Saccharomyces cerevisiae,* or baker's yeast, as a host for the recombinant DNA-mediated expression of a variety of foreign polypeptides. However, the distinctions among other species of the genus Saccharomyces are not always well-defined. Many of these species are capable of interbreeding with *S. cerevisiae* and are likely to possess regulatable promoters which are analogous or identical to promoters in *S. cerevisiae*, including but not limited to GAL10, ADH2, and/or alpha mating factor promoters. Therefore, it will be obvious to those skilled in the art that, for the expression of pre-S-containing polypeptides, the selection of a host strain extends to other species of the genus Saccharomyces, including but not limited to *carlsbergensis, uvarum, rouxii, montanus, kluyveri, elongisporus, norbensis, oviformis*, and *diastaticus.*

Several yeast genera, such as Hansenula, Candida. Torulopsis, and Pichia, have been shown to contain similar metabolic pathways for the utilization of methanol as a sole carbon source for growth. The gene for alcohol oxidase, an enzyme which participates in this metabolic pathway, has been isolated from *Pichia pastoris.* The *P. pastoris* alcohol oxidase promoter has been isolated and shown to be susceptible to methanol induction of expression. Such an inducible promoter is useful for the expression of polypeptides which are negatively selected in yeast. In particular, this promoter has been shown to be active on a plasmid for the inducible expression of the S domain in *P. pastoris* in particulate form. This observation highlights the ability of other yeast genera to function as hosts for the recombinant DNA-mediated expression of S polypeptides in immunologically active form. Therefore, it will be obvious to those skilled in the art that, for the expression of pre-S-containing polypeptides such as PreS-1/S-2/S protein, the selection of a host strain extends to species from other genera of yeast from the Families Saccharomycetaceae and Cryptococcaceae, including, but not limited to Pichia, Candida, Hansenula. Torulopsis, Kluyveromyces, and Saccharomycopsis.

In the process of purifying MB surface antigen, excessive instability and breakdown of the surface antigen has been observed. To combat this, solvents are typically buffered and also contain protease inhibitors such as PMSF and EDTA. To further reduce proteolysis, it is preferred to carry out all purification steps at about 4° C.

Typical protease inhibitors suitable for the procedures and protocols of this invention include but are not limited to metal-chelating agents, heavy metal ions, SH blocking reagents, substrate-like compounds of proteases or polypeptides that inhibit proteases. Some useful protease inhibitors are provided as follows:

$Ag^{++}$, $Hg^{++}$, $Cu^{++}$ and other heavy metal ions
antithrombin III
antithrombin III - heparin
$\alpha_1$-antitrypsin
aprotinin
basic amino acids
benzamidine
bestatin
$\alpha,\alpha'$-bipyridyl, Na-fluoride
4-bromo-phenacyl bromide chicken egg white trypsin inhibitor
chymostatin
citrate
cysteine
4-dinitrophenol diethylphosphate
DFP (diisopropylphosphofluoridate)
DTT
E-64 (Boehringer Mannheim)
EDTA and other chelating agents
formaldehyde
guanidinium chloride
heparin
hirudin
4-hydroxymercuribenzoate
iodoacetamide
iodoacetic acid
leupeptin
$\alpha_2$-macroglobulin
mercaptoethanol
p-mercuribenzoate
mercuric chloride
$\alpha$-microglobulin
$\alpha$-N-(p-nitrobenzyl-oxycarbonyl)-L-arginyl-chloromethyl ketone
oxalate
pepstatin from a variety of sources, including Streptomyces
1,10-phenanthroline
2-phenanthroline
phenothiazine-N-carbonyl chloride
phosphoramidone
PMSF
pryrophosphate
SH-blocking reagents
silver nitrate
soybean trypsin inhibitor
p-toluene sulfonyl fluoride
TLCK(L-1-chloro-3-(4-tosylamido)-7-amino-2-heptanone-hydrochloride
TPCK(L-1-chloro-3-(4-tosylamido)-4-phenyl-2-butanone
trypsin inhibitor from hen egg
ZPCK (benzyloxycarbonyl-L-phenylalanine)

Buffered solutions containing one or more of the listed inhibitors may be adapted to one or more steps in the process of purifying MB surface antigen.

Yeast cells transformed with expression vectors coding for preS-1/S-2/S protein or variants thereof, are grown and harvested. If storage of the cells is desired, the cells are then washed in buffer, e.g. PBS, to form a cell paste. Storage of the cell paste is typically done by freezing in liquid $N_2$.

Purification typically begins as follows. A batch of frozen cell paste is thawed and suspended in buffer containing proteolytic inhibitors, e.g. PBS in 1 mM PMSF. Cells are then disrupted, preferably by mechanical means, such as a Stansted Cell Disrupter (Stansted Fluid Power LTD.), a Dyno-Mill (Willy A. Bachofen Manufacturing Engineers), or a Laboratory Homogenizer (Gaulin Corporation). The gentle bead breakage method for disruption has been found unsuitable for scale-up. Disruption by a Stansted Cell Disrupter is the most preferred because of its rapid operation.

Yeast cell disruption results in a crude extract. It is necessary at this point to remove cell debris in the extract so that mechanical clogging in subsequent purification steps is avoided. Centrifugation at about 4,400×g for 5 minutes has been found adequate, but it is readily understood that different centrifugation speeds for different times are also possible and easily rendered operable Ultracentrifugation of the supernatant at 130,000×g for one hour generally pellets the MB surface antigen associated with the yeast membrane, and serves as a useful method of testing for the presence of MB surface antigen after the centrifugation of the crude cell extract. The presence of pre-S polypeptide epitopes can be ascertained by the binding of these epitopes to polymerized human serum albumin (PHSA) in a sandwich RIA assay with labelled antibody specific to HBV surface antigen.

Further steps in the purification process are performed on the 4,400×g supernatant remaining after the cell debris is removed from the crude extract by centrifugation at 4,400×g for 5 minutes, as described above.

The next step is performed to remove any remaining soluble material. The soluble fraction in the 4,400×g supernatant is conveniently removed by ultracentrifugation, filtration, diafiltration, with or without pressure, as the case may be. Buffers should contain inhibitors of proteases. The preferred method of removing the soluble fraction is to pump the 4,400 ×g supernatant through a Minikros® diafiltration unit of 0.2 μm pore size (Microgon, Inc.) under positive pressure of about 10–15 psi, with a wash of 1 mM PMSF in PBS. The pressure Promotes passage of soluble material through the membrane barrier of the diafiltration unit. The practical advantage of diafiltration is that dialysis and filtration are performed together. Other types of diafiltration units are feasible for use, e.g. KrosFlo® of Microgon, Inc., or any one of a variety of hollow fiber cartridges of Amicon or A/G Technology. Release of soluble material can be monitored by optical density.

To prepare washed yeast membranes, the membrane-bound material is treated with mild denaturing agents at concentrations sufficient to release most of the MB protein without release of the MB surface antigen. Suitable agents include detergents or protein denaturants, or mixtures thereof. A variety of neutral or nonionic detergents can be used, including but not limited to detergents of the monoxynol series (TRITON N), octoxynol series (TRITON X-100), polyoxyethylene alcohol series (BRIJ), polyoxyethylene (20) sorbitan monooleate series (TWEEN) or Emasol series, deoxycholate, octylglucopyranoside or Nonidet NP-40. Zwitterionic detergents such as CHAPS or CHAPSO are also useful and suitable agents.

Protein denaturants that are suitable for releasing unwanted or undesired MB proteins include the generic class of compounds of the formula:

wherein

R is amino, loweralkylthio, loweralkyloxy, or sulfur;
X is amino, sulfur or oxygen; and
Y is hydrogen or amino.

This formula includes the preferred protein denaturant, guanidine.HCl, most preferably used in a concentration gradient from between about 7M to about 1M. Additional suitable protein denaturants include anions such as $ClO_4^-$ and chaotropic agents.

The preferred protocol for preparing washed yeast membrane is to conduct diafiltration of the membrane-bound material with about 0.2 mM PMSF and about 1 mM EDTA in PBS, followed by a wash of about 7M guanidine.HCl, then many washes of about 1M guanidine.HCl.

Washed yeast membranes are then extracted with a detergent or a protein denaturant, or mixtures thereof, with the purpose of releasing MB surface antigen. Any one of a variety of nonionic or neutral detergents are suitable for the extraction, including but not limited to detergents of the monoxynol series (TRITON N), octoxynol series (TRITON X-100), polyoxyethyelne alcohol; series (BRIJ), polyoxyethylene (20) sorbitan monooleate series (TWEEN), Emasol series, deoxycholate, octylglucopyranoside or Nonidet NP-40. Suitable zwitterionic detergents include CHAPS or CHAPSO. The preferred detergent is Triton X-100 at concentrations between about 2% (w/v) and about 0.05% (w/v), most preferably between about 1% (w/v) and 0.1% (w/v).

Protein denaturants that are suitable for releasing MB surface antigen include the generic class of compounds of the formula:

wherein

R is amino, loweralkylthio, loweralkyloxy, or sulfur;

X is amino, sulfur or oxygen; and

Y is hydrogen or amino.

This formula includes the preferred protein denaturant, guanidine.HCl at a concentration of about 1M. Additional suitable protein denaturants include anions such as ClO$_4^-$ and chaotropic agents. A solution containing 3M KSCN has been found to be operable, except that subsequent diafiltration steps must be performed by ultracentrifugation.

The procedure for extracting or releasing MB surface antigen from the washed yeast membrane may require more than one washing or extraction step. Applicants prefer the steps of (a) incubation of the washed yeast membrane at 4° C. in 0.5% (w/v) Triton X-100 in 1M guanidine.HCl, to release MB surface antigen;

(b) diafiltration with 0.1% (w/v) Triton X-100 in 1M guanidine.HCl, to promote passage of the released surface antigen across the membrane of the diafiltration unit;

(c) concentration of the filtrate by either ultrafiltration or ultracentrifugation; and (d) incubation of the concentrated filtrate in 5 mM DTT for 5 minutes, followed by diafiltration against 2 mM DTT in 1M guanidine.HCl, then against PBS to remove residual impurities.

Alternatively, the guanidine.HCl of step (a) may be substituted with protease inhibitor(s) effective to inhibit the endogenous proteolytic activity, e.g., a final concentration of 0.2 mM PMSF, 10 mM EDTA, 0.1% (w/v) pepstatin A, 0.013% (w/v) aprotinin and 10mM benzamidine.HCl, all in the same extraction buffer.

Extracting or releasing MB surface antigen from washed yeast membrane need not require diafiltration. Centrifugation and dialysis are also useful alternative procedures provided that appropriate detergents or denaturants are employed. It is contemplated that steps (a)-(d) may be varied substantially. One or more additional concentration steps may be required, as the case may be.

It will be readily apparent that the procedures and protocols of this invention may be modified or varied by, for example, one or more additional steps such as hydrophobic chromatography, solid-phase chromatography with e.g. silica gel, precipitation with salts such as ammonium sulfate, ion-exchange chromatography, immunoaffinity chromatography or any other technique useful for the Purposes of recombinant protein purification.

Analysis of the purified antigen by electron microscopy showed that, for all the lots except those involving KSCN extraction, no particles of about 20 nm in diameter were detected. Most lots contained a heterogeneous population of particles, including vesicle-like structures, large aggregates and some circular particles of about 14-25 nm diameter.

EXAMPLE 1

A. Materials and Methods

The following were purchased from commercial sources: guanidine. HCl, Schwartz/Mann Biotech; TRITON X-100, Fisher Scientific Company; dithiothreitol, Bio-Rad; MINIKROS 0.2 μm Module (1 ft.²), Microgon Inc.; Amicon hollow fiber cartridge (HIP 100-20), Amicon.

Throughout this application, glycoprotein was determined by the periodic acid-Schiff base procedure of Neville, D. M. et al., *Methods in Enzymology* 32 92 (1974). Protein concentrations were determined by the SDS-Lowry assay, e.g. Lowry, O. H. et al., *J. Biol. Chem.* 193 265 (1951); and the Coomassie blue-binding assay, e.g. Bradford, M. M., *Anal. Biochem.* 72 248 (1976). Western blotting was conducted substantially by the procedures of Burnette, W. N., *Anal. Biochem.* 112 195 (1981).

Immunochemical tests were performed on the lots purified according to the following procedures. Binding to polymerized human serum albumin was conducted according to Valenzuela et. al., *Biotechnology*, 3 317 (1985), and the results summarized in Table VIII. Immunochemical determinants were assayed by a procedure adapted from AUSRIA® II-125 (Abbott Labs), wherein $^{125}$I-labelled antibody specific for surface antigen is bound to a specific antigen-antibody complex bound to a solid phase. Biological activity was tested by the mouse potency test.

B. Expression of PreS-1/S-2/S Antigen

A yeast vector, YADH2/PSSC-1, was constructed with the alcohol dehydrogenase II (ADH2) promoter and the HBV preS-1/S-2/S DNA sequence. Yeast *Saccharomyces cerevisiae* strain 2150-3-2 was transformed with YADH2/PSSC-1, and the cells were grown and harvested. Details of the construction of the vector and its transformation are found in U.S. application Ser. No. 824,405, filed Jan. 31, 1986, incorporated by reference for these purposes. Cells were washed in phosphate buffered saline (PBS) and the cell paste was frozen in liquid N$_2$.

C. Purification of Antigen, Lot PS-16

All purification steps of this section C were conducted at 4° C. Frozen cell Paste (100 g) of the antigen synthesizing yeast cells was suspended in 200 ml of PBS containing 1 mM phenylmethylsulfonylfluoride (PMSF), and the cells were disrupted by two passes through a STANSTED CELL DISRUPTER. The resulting crude extract was centrifuged for 5 minutes at 4,400×g to remove cell debris. The 4,400×g supernatant was further centrifuged at 100,000×g for one hour and the precipitate (yeast membrane fraction) was separated from the soluble fraction. Localization of the recombinant preS-1/S-2/S hepatitis B antigen was performed by a polymerized human serum albumin binding radioimmunoassay. The principle of the assay is to measure binding of the preS-2 region to polymerized human serum albumin coated on beads by a sandwich type RIA test. The coated beads are incubated with the sample containing unknown quantities of preS-2 polypeptides, washed, and then incubated with $^{125}$I-labelled antibody specific to HBV surface antigen. The beads are counted after rewashing. The results for one 36 gram batch are presented in Table I.

TABLE I

EFFECT OF CENTRIFUGATION ON LOCALIZATION OF RECOMBINANT PRES-1/S-2/S HEPATITIS B ANTIGEN IN YEAST

| Preparation | pHSA Binding RIA mg | Protein mg | Specific Activity μg RIA activity/mg protein* |
|---|---|---|---|
| 4,400 × g supernatant | 3.2 | 3,600 | 0.9 |
| yeast membrane fraction | 3.2 | 320 | 10 |
| soluble fraction | 0.51 | 2,800 | 0.2 |
| cell debris | 0.45 | 450 | 1.0 |

*defined as μg of pHSA binding RIA/mg protein

Table I demonstrates that the presence of the preS-2 polypeptide was predominantly concentrated in the yeast membrane protein. Further manipulations were preformed on the 4,400×g supernatant to avoid the 100,000×g centrifugation step.

(a) Preparation of washed yeast membrane

The 4,400 ×g supernatant was introduced under positive pressure of 10–15 psi into a diafiltration unit (450 ml capacity) equipped with a hollow fiber membrane (MINIKROS, 0.2 μm, 1 ft.[2]) with a peristaltic pump. Diafiltration with 2.5L of PBS containing 0.2 mM PMSF and 1 mM EDTA, followed by 250 ml of 7M guanidine HCl and 3L of 1M guanidine HCl, removed membrane bound yeast impurities without removal of the antigen from the membrane. The resulting retentate product was purified antigen bound to membranes (washed yeast membrane).

(b) Extraction of antigen from yeast membrane

Washed yeast membranes, the product of paragraph (a) of Example 1C, supra, were incubated for 20 minutes at 4° C. in 1L of 0.5% (w/v) Triton X-100 in 1M guanidine HCl. The solubilized antigen was separated from the yeast membrane by concentration to 200 ml over a hollow fiber unit (MINIKROS, 0.2 μm) followed by diafiltration of the yeast membrane with 1.5L of 0.1% (w/v) Triton X-100 in 1M guanidine HCl. The filtrate contained the antigen and was concentrated over a hollow fiber membrane (AMICON, 100,000 NMW, 0.6 ft.[2]) to 200 ml, incubated in 5 mM DTT for 5 minutes, and then diafiltered with 1L of 2 mM DTT in 1M guanidine HCl followed by 2L of PBS. The resulting purified antigen (designated PS-16) had a high specific activity, as demonstrated by the results of Table II.

TABLE II

PURIFICATION OF MEMBRANE-BOUND RECOMBINANT PRES-1/S-2/S HEPATITIS B ANTIGEN FROM YEAST BY RELEASE FROM THE MEMBRANE IN PRESENCE OF 0.5% TRITON X-100[1]

|  | pHSA Binding RIA mg | Protein mg | Specific Activity μg RIA activity/mg protein |
|---|---|---|---|
| crude extract | >12 | 9,700 | >1.2 |
| 4,400 × g supernatant | 16 | 5,800 | 2.8 |
| washed yeast membrane | 8.3 | 240 | 34 |
| purified antigen (PS-16) | 2.9 | 63 | 46 |

[1]Antigen lot number PS-16.

A portion of the purified antigen was then treated with 3M KSCN in PBS for 16 hours and diafiltered over a hollow fiber membrane (Amicon, 100,000 NMW, 0.6 ft.[2]) with 5 vol. of 3M KSCN in PBS and 10 vol. of PBS, yielding lot number PS-16/KSCN.

EXAMPLE 2, Lot PS-17

The procedure of Example 1 was repeated, except that the step (b) of 1C, wherein 0.5% (w/v) Triton X-100 in 1M guanidine HCl is used to obtain release of surface antigen from yeast membrane, is replaced by 1% (w/v) Triton X-100 in 1M guanidine HCl. The resulting protein product is substantially pure recombinant preS-1/S-2/S surface antigen, having lot number PS-17.

EXAMPLE 3, Lot PS-12

Another batch of 100 g of frozen cell paste of antigen synthesizing yeast cells was suspended in 200 ml of PBS containing 1 mM PMSF, and the cells were disrupted by two passes through a Stansted Cell. The crude extract was centrifuged for 5 minutes at 4,400×g to remove cell debris. The 4,400×g supernatant was introduced under positive pressure of 10-15 psi into a diafiltration unit (450 ml capacity) equipped with a hollow fiber membrane (MINIKROS, 0.2 μm, (0.2 μm, 1 ft.[2]) with a peristaltic pump. Such diafiltration against 2.5 L of PBS containing 0.2 mM PMSF and 1mM EDTA, followed by 250 ml of 7M guanidine HCl and 3L of 1M guanidine HCl, removed membrane-bound yeast impurities without removal of the antigen from the membrane. The retained membrane-bound protein was then ultracentrifuged at 130,000×g for 60 minutes, the precipitate resuspended in PBS to yield the washed membrane fraction. Specific activity for various stages of the protocol of Example 3 was determined, the results presented in Table IV.

EDTA, followed by 300 ml of 6M guanidine.HCl, then 2L of 1M guanidine.HCl, and finally 1.5 L of PBS con-

TABLE IV

ISOLATION OF RECOMBINANT PRES-1/S-2/S HEPATITIS B ANTIGEN FROM YEAST:
EFFECT OF ULTRA CENTRIFUGATION OF WASHED YEAST MEMBRANE

|  | pHSA Binding RIA µg | Protein mg | Specific Activity µg RIA activity/mg protein |
|---|---|---|---|
| crude extract | 6,200 | 10,400 | 0.6 |
| 4,400 × g supernatant | 6,480 | 8,700 | 0.7 |
| washed membrane fraction | 5,400 | 230 | 24 |

An aliquot of the washed membrane fraction was then subjected to extraction with 600 ml of 3M KSCN in PBS for 40 minutes, followed by another round of ultracentrifugation at 130,000×g for 60 minutes, and the supernatant was concentrated over an Amicon hollow fiber membrane (100,000 NMW, 0.6 ft$^2$) to 200 ml, then diafiltered with 1 L of 3MKSCN in PBS followed by 2 L of PBS, yielding lot no. PS-12. Results are given in Table V.

TABLE V

EFFECT OF 3M KSCN EXTRACTION OF THE WASHED MEMBRANE FRACTION

|  | pHSA Binding RIA mg | Protein mg | Specific Activity µg RIA activity/mg protein |
|---|---|---|---|
| Washed membrane fraction | 730 | 36 | 20 |
| Retentate (PS-12) | 200 | 11 | 18 |
| Precipitate[1] | 220 | 18 | 12 |

[1] i.e. the precipitate after the final ultracentrifugation at 130,000 × g. This precipitate was resuspended in PBS before assay.

EXAMPLE 4, Lot PS-15

The procedure of example 3 was repeated except that the final diafiltration step was performed with 1 L of 2 mM DDT in 2M Urea followed by 2 L of PBS, yielding purified antigen lot no. PS-15. Results are in Table VI.

TABLE VI

| Preparation | pHSA Binding RIA mg | Protein mg | Specific Activity µg RIA activity/mg protein |
|---|---|---|---|
| crude extract | 23 | 9,200 | 2.5 |
| 4,400 supernatant | 22 | 7,000 | 3.2 |
| washed yeast membrane | 21 | 270 | 77 |
| purified antigen (PS-15) | 0.44 | 19 | 23 |

EXAMPLE 5, Lot PS-48

Frozen cell paste (90 g) of the antigen synthesizing yeast cells was suspended in 90 ml of PBS containing 1.0 mM PMSF 10 mM EDTA and 0.1 M Tris.HCl, pH 7.5 ("buffer"). The cells were broken in a DYNO-MILL, 5 times for 30 seconds, the cell paste was diluted with 1.4 L buffer and then removed from the DYNO-MILL. The resulting crude extract was centrifuged for 10 minutes at 4,400×g to remove cell debris. The 4,400×g supernatant was introduced under positive presence of 10-15 psi into a diafiltration unit (450 ml capacity) equipped with a hollow fiber membrane (MINIKROS, 0.2 µm, 1 ft$^2$) with a peristaltic pump, and diafiltered with 1.5L of PBS containing 0.2 mM PMSF and 10mM EDTA, followed by 300 ml of 6M guanidine.HCl, then 2L of 1M guanidine.HCl, and finally 1.5 L of PBS containing 0.2 mM PMSF and 10mM EDTA. The resulting retentate (washed yeast membrane) was incubated for 20 minutes at 4° C. in 1.6L of PBS containing 0.4% Triton X-100 and protease inhibitors [final concentrations in PBS of 0.2 mM PMSF, 10 mM EDTA, 0.1% (w/v) pepstatin A, 0.013% (w/v) aprotinin and 10mM benzamidine.HCl]. The solubilized antigen was separated from the yeast membrane by concentration to 200 ml over a hollow fiber unit (MINIKROS, 0.2 µm) followed by diafiltration of the yeast membrane with 1.5L of 10 mM sodium phosphate buffer, pH 7.5, containing 0.1% (w/v) Triton X-100 and the above protease inhibitors. The filtrate contained the antigen, was concentrated over a hollow fiber membrane (AMICON) (100,000 NMW 0.6 ft$^2$) to 200 ml, then diafiltered against 7 volumes of PBS. The retentate, which contained the antigen, was incubated in 5 mM DTT in 4M Urea for 15 minutes, then concentrated over a hollow fiber membrane (AMICON) (100,000 NMW, 0.6 ft$^2$) to 200 ml, and as a final step was diafiltered against 5 volumes of 2 mM DTT in 2M Urea, then 10 volumes of PBS, yielding purified antigen (PS-48). Results are summarized in Table VII.

TABLE VII

| Preparation | pHSA Binding RIA mg | Protein mg | Specific Activity µg RIA activity/mg protein |
|---|---|---|---|
| crude extract | 17.9 | 14,400 | 1.2 |
| 4,400 × g supernatant | 18.6 | 14,800 | 1.3 |
| washed yeast membrane | 3.1 | 508 | 6.0 |
| purified antigen* (PS-48) | 2.5 | 67 | 38 |

*This sample was also measured to have a specific activity of 2.9 µg AUSRIA ®/mg protein.

The immunological characteristics of each lot are summarized in Table VIII. Additional evidence suggests that the low AUSRIA ® values are attributable to the masking of antigenic determinants by the preS-1 region polypeptide.

TABLE VIII

IMMUNOCHEMICAL AND BIOLOGICAL
CHARACTERISTICS OF VARIOUS LOTS
RIA Specific Activity
RIA Activity μg/mg Protein

| Lot Number | by pHSA Binding Assay | by AUSRIA | R.P.[b] |
|---|---|---|---|
| PS-12 (Example 3) | 15 | <0.4 | 0.183[a] |
| PS-15 (Example 4) | 23 | <0.06 | 0.0189[a] |
| PS-16 (Example 1) | 46 | 4.1 | 0.0067 |
| (PS-16)[a] | ND | 3.9[a] | 0.0193[a] |
| PS-16/KSCN (Example 1) | 26 | 2.1 | 0.0126 |
| (PS-16/KSCN)[a] | ND | 1.6[a] | 0.0256[a] |
| PS-17 (Example 2) | 50 | 5.1 | 0.0125 |
| PS-48 (Example 5) | 38 | 2.9 | ND |

ND = Not determined
[a]To solubilize the antigen urea was added to a final concentration of about 0.4M–0.6M before assay.
[b]R.P. = relative potency, a combined measure of antibody concentration, specificity and affinity, and is defined as follows:

$$\frac{50\% \text{ End Point of Sample/Lowry Protein}}{50\% \text{ End Point of Standard/Lowry Protein}},$$

wherein the end point of the sample is the concentration of the antigen that binds a standard and constant concentration of antibody raised against that particular antigen, as calculated by antibody use determination, Logit transformed percent maximum bound analysis.

The results of the pHSA binding assay and AUSRIA indicate that PS-16 and PS-17 are the preferred lots for vaccination purposes.

EXAMPLE 7

In Vivo Studies

Four Rabbits were each inoculated with PS-16 adsorbed to Alhydrogel in doses of 20 μg I.M., according to the following schedule:

| Day | Method |
|---|---|
| −8 | prebleed |
| 0 | inoculate PS-16 with Alhydrogel 20 μg I.M. |
| 27 | inoculate PS-16 with Alhydrogel 20 μg I.M. |
| 27 | bleed |
| 41 | inoculate PS-16 with Alhydrogel 20 μg I.M. |
| 41 | bleed |
| 76 | inoculate PS-16 with Alhydrogel 20 μg I.M. |
| 76 | bleed |

Circulating antibodies were tested with the following results:

PS-16, Rabbits #227, 228, 229 and 230
Reciprocal Titers

| | R227 | R228 | R229 | R230 |
|---|---|---|---|---|
| Anti-S (AUSAb) | | | | |
| Day −8, preimmune | <8 | <8 | 36 | 36 |
| 41 | 160 | 720 | 540 | 1580 |
| 76 | 720 | 2350 | 160 | 160 |
| Anti-S2 (ELISA) | | | | |
| Day −8, preimmune | <10 | <10 | <10 | <10 |
| 41 | 320 | 160 | 320 | 80 |
| 76 | 1280 | 1280 | 1280 | 640 |
| Anti-S1 (ELISA) | | | | |
| Day −8, preimmune | <10 | <10 | <10 | <10 |
| 41 | 80 | 640 | 40 | 320 |
| 76 | 40 | 20 | 160 | 80 |

EXAMPLE 8

Lot No. PS-16, the sample prepared by the procedure of Example 1C, contained antigen complexes having MW>$10^6$. A sample of the lot was subjected to SDS polyacrylamide gel electrophoresis according to the method of Laemmli, U.K. *Nature* 227 680 (1970). Lot No. PS-16 was found to contain substantially pure polypeptide subunits with Mr at positions corresponding to about 39,000 daltons and 45,000 daltons. Periodic acid-Schiff base staining procedure showed that the subunit migrating at 45,000 daltons was a glycoprotein. Western blotting indicated that both subunits possessed immunological determinants of the preS-1 sequence, the preS-2 sequence and the S protein.

It is concluded that the larger subunit migrating at 45,000 daltons is the glycosylated form of the 39,000 dalton subunit.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims.

What is claimed is:

1. A method of substantially purifying recombinant preS-1/S-2/S hepatitis B antigen, or portion thereof, from yeast membranes, comprising the steps of
   a) taking a portion of yeast membrane associated antigen extract;
   b) removing the debris of the extract of step (a) by centrifugation;
   c) subjecting the supernatant to diafiltration under positive pressure between about 10 psi and about 15 psi, in the presence of a solution effective to release undesired yeast membrane-bound proteins, said solution comprising guanidine.HCl in concentrations varying during said diafiltration from between about 7M to about 1M, and thereafter removing said undesired yeast membrane-bound proteins to yield washed yeast membranes as a retentate product;
   d) subjecting the retentate product of step (c) to a second solution effective to release the membrane bound surface anitgen, said second solution comprising octoxynol-9.5 at a concentration of between about 0.1% (w/v) and about 1.0% (w/v);
   e) separating the surface antigen released in step (d) from yeast membrane, by diafiltration in the presence of a third solution effective to promote passage of said surface antigen across the diafiltration membrane; and
   f) subjecting the filtrate of step (e) to diafiltration to remove low molecular weight impurities, resulting in a substantially purified recombinant preS-1/S-2/S hepatitis B antigen, or portion thereof.

2. The method of claim 1, wherein the second solution in step (d) comprises about 0.5% (w/v) octoxynol-9.5 in about 1M guanidine.HCl.

3. The method of claim 1, wherein the second solution in step (d) comprises about 1% (w/v) octoxynol-9.5 in about 1M guanidine.HCl.

4. The method of claim 1, wherein the second solution in step (d) comprises octoxynol-9.5 at concentrations between about 0.1% (w/v) and about 1% (w/v), and about 1M guanidine.HCl.

5. The method of claim 1, wherein the second solution comprises buffer, octoxynol-9.5 in a concentration range of between about 1% (w/v) and about 0.1% (w/v), and protease inhibitors.

6. The method of claim 1, wherein said second solution consists essentially of PBS containing about 0.4% (w/v) octoxynol-9.5, about 0.2 mM PMSF about 10 mM EDTA, about 0.1% (w/v) pepstatin A, about 0.013% (w/v) aprotinin, and about 10 mM benzamidine.HCl.

7. The method of claim 1, wherein said third solution of step (e) comprises about 0.1% (w/v) Triton X-100 in 1M guanidine-HCl.

8. The method of claim 1, wherein said third solution of step (e) comprises a buffered solution containing 0.1% (w/v) Triton X 100.

* * * * *